(12) United States Patent
Nasiri et al.

(10) Patent No.: US 10,116,163 B2
(45) Date of Patent: Oct. 30, 2018

(54) UNINTERRUPTIBLE POWER SUPPLY (UPS) DIRECT CURRENT (DC) LOAD LEVELING

(71) Applicants: General Electric Company, Schenectady, NY (US); UWM Research Foundation, Inc., Milwaukee, WI (US)

(72) Inventors: Adel Nasiri, Mequon, WI (US); Seyed Ahmad Hamidi, Milwaukee, WI (US); Russell Wayne Hum, Waukesha, WI (US); John Ferdinand Bopp, West Bend, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 267 days.

(21) Appl. No.: 15/076,358

(22) Filed: Mar. 21, 2016

(65) Prior Publication Data

US 2017/0085122 A1 Mar. 23, 2017

Related U.S. Application Data

(60) Provisional application No. 62/220,670, filed on Sep. 18, 2015.

(51) Int. Cl.
| | |
|---|---|
| *H02J 7/00* | (2006.01) |
| *H02J 9/00* | (2006.01) |
| *H02J 9/06* | (2006.01) |
| *A61B 6/00* | (2006.01) |
| *A61B 6/03* | (2006.01) |

(52) U.S. Cl.
CPC ............. *H02J 9/061* (2013.01); *A61B 6/032* (2013.01); *A61B 6/56* (2013.01)

(58) Field of Classification Search
CPC ............. A61B 6/032; A61B 6/56; H02J 9/061
USPC ........................................ 307/66; 378/4, 103
See application file for complete search history.

(56) References Cited

U.S. PATENT DOCUMENTS

| | | | |
|---|---|---|---|
| 7,683,575 B2 | 3/2010 | Berdichevsky et al. | |
| 7,796,736 B2 | 9/2010 | Kasuya | |
| 2010/0188875 A1* | 7/2010 | Kalms | H02J 1/06 363/34 |
| 2011/0175451 A1* | 7/2011 | Moon | H02J 9/062 307/66 |
| 2012/0027161 A1* | 2/2012 | Abenaim | A61B 6/027 378/4 |
| 2013/0134924 A1* | 5/2013 | Kanakasabai | B60L 1/003 320/104 |
| 2015/0036786 A1 | 2/2015 | Katcha et al. | |

* cited by examiner

Primary Examiner — Thomas Skibinski
(74) Attorney, Agent, or Firm — Fletcher Yoder, P.C.

(57) ABSTRACT

A system includes an AC-DC converter configured to convert power from an AC supply to a DC bus to provide a first portion of power a medical imaging load. The system includes an uninterruptible power supply (UPS) coupled to the DC bus. The UPS comprises at least one battery cell and a DC-DC converter comprising one or more switches and coupled between the at least one battery cell and the DC bus. The system includes a control system comprising a processor configured to send one or more signals to control operation of the one or more switches to cause the DC-DC converter to control power discharged from the at least one battery cell to the DC bus to provide a second portion of power to the medical imaging load.

20 Claims, 6 Drawing Sheets

UNINTERRUPTIBLE POWER SUPPLY (UPS) DIRECT CURRENT (DC) LOAD LEVELING

CROSS-REFERENCE TO RELATED APPLICATION

This application claims priority from and the benefit of U.S. Provisional Application Ser. No. 62/220,670, entitled "UNINTERRUPTIBLE POWER SUPPLY (UPS) DC LOAD LEVELING", filed Sep. 18, 2015, which is hereby incorporated by reference in its entirety.

BACKGROUND

The subject matter disclosed herein relates to power supplies, and more particularly, to an uninterruptible power supply with load leveling for medical imaging loads.

Uninterruptable Power Supply (UPS) systems may be utilized as backup power for electrical systems, providing emergency power when a main power source fails. That is, UPS systems may provide uninterruptible and reliable electrical power for systems with loads in which a continuous and reliable power supply is desirable. Examples of such systems include healthcare systems, medical facilities, and data centers. For instance, a UPS system may protect a medical imaging system of a medical facility against any electrical power disturbances or outages from the main source.

Since conventional UPS systems are designed to meet a demand of peak power of the medical imaging system, the UPS system may take up large amounts of space and be expensive. Moreover, the UPS system may be used with an infrastructure that is designed to provide peak power of the medical imaging system because the UPS is primarily used during outages and/or power disturbances. However, medical imaging systems may be desired in medical facilities that do not have power infrastructure designed to meet the demand of peak power of the medical imaging systems. That is, the medical imaging facility may be designed to receive power rated lower than the power desired to operate the medical imaging system. For the preceding reasons, there is a need to improve UPS systems used with medical imaging systems.

BRIEF DESCRIPTION

Certain embodiments commensurate in scope with the originally claimed disclosure are summarized below. These embodiments are not intended to limit the scope of the claimed disclosure, but rather these embodiments are intended only to provide a brief summary of possible forms of the disclosure. Indeed, embodiments may encompass a variety of forms that may be similar to or different from the embodiments set forth below.

In a first embodiment, a system includes an alternating current (AC)-direct current (DC) converter configured to convert power from an AC supply to a DC bus to provide a first portion of power a medical imaging load, an uninterruptible power supply (UPS) coupled to the DC bus, wherein the UPS includes at least one battery cell, and a DC-DC converter including one or more switches and coupled between the at least one battery cell and the DC bus, and a control system comprising a processor configured to send one or more signals to control operation of the one or more switches to cause the DC-DC converter to control power discharged from the at least one battery cell to the DC bus to provide a second portion of power to the medical imaging load.

In a second embodiment, a system configured to provide power to a medical imaging load includes an uninterruptible power supply (UPS) configured to couple to a direct current (DC) bus, including at least one battery cell, and a DC-DC converter configured to convert power from a supply that supplies power to the medical imaging load, via the DC bus, to charge the at least one battery cell and to convert power from the at least one battery cell to discharge power to provide additional power to the medical imaging load.

In a third embodiment, a method of manufacturing a medical imaging load includes electrically coupling a direct current (DC) bus to a medical imaging load, electrically coupling the DC bus to an alternating current (AC)-DC converter configured to convert power from an AC supply to the DC bus to provide a first portion of power to the medical imaging load, and electrically coupling an uninterruptible power supply (UPS) to the DC bus, wherein the UPS comprises at least one battery cell and a DC-DC converter includes one or more switches, and wherein the DC-DC converter is configured to control power discharged from the at least one battery cell to the DC bus to provide a second portion of power to the medical imaging load corresponding to a pulsed load profile of the medical imaging load.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
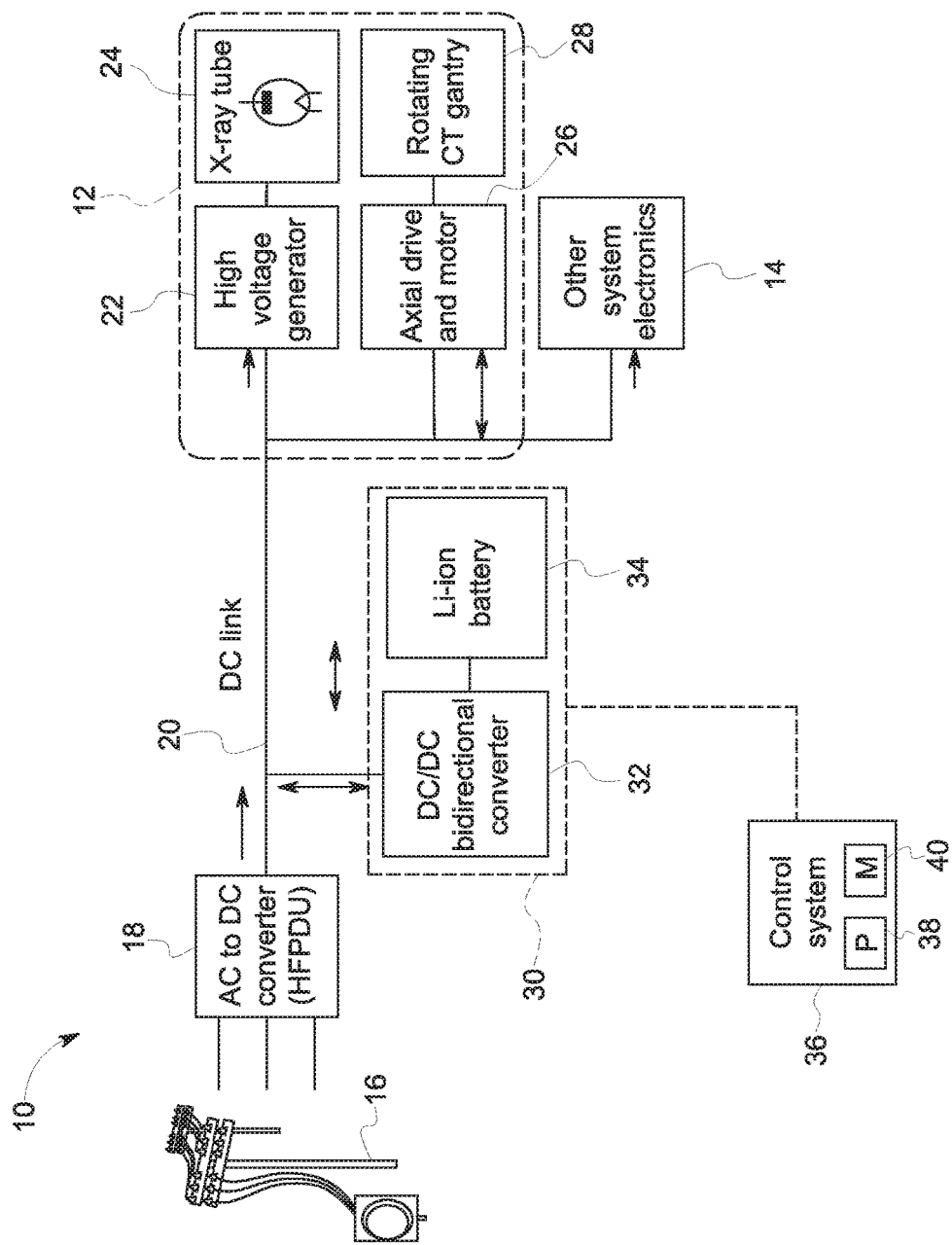
FIG. 1 is a block diagram of a power supply system having a DC line-interactive uninterruptable power supply (UPS) for a medical imaging load, in accordance with an embodiment.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean Systems and methods described herein are related to medical imaging systems that use an uninterruptible power supply (UPS). Conventional medical imaging systems typically use a UPS to continue operation during electric power disturbances or outages. The power line and the UPS are typically rated to deliver peak power to the one or more loads. In the event the main source from the power line fails, the UPS provides power to the medical imaging system. For example, the UPS may provide power to an X-ray scanner to enable the X-ray scanner to continue operation during a power outage.

However, because the UPS may be designed for the peak power rating of the medical imaging system, the UPS may take up space and be expensive. That is, the UPS may be rated at the peak rating of the medical imaging system, which is greater than the average power rating consumed by the medical imaging system. For instance, the peak power of a computed tomography (CT) system may be nearly 150 kVA while the average power is less than 10 kW. As such, to design the UPS at peak rating means higher total cost and required space for the power supply section of the machine.

Moreover, the UPS system may be used with an infrastructure that provides peak power to the medical imaging system because the UPS is primarily used during outages and/or power disturbances. That is, the power line may be rated to provide the desired power for the load, using the UPS in the event of an outage. As such, medical imaging systems are installed in areas where power rating of the medical imaging system is satisfied by the power line.

Additionally, various topologies of UPS systems may be used to provide power during power disturbances and outages. The topologies of alternating current (AC) based UPS systems may include off-line, online, line-interactive and series-parallel line-interactive topologies. An off-line UPS topology (i.e. a standby topology) may include a simple design, a small size, and passive line conditioning, but may include long switching times, poor performance with non-linear loads, and no output voltage regulation. An online UPS topology may provide power conditioning, load protection, and better performance than the off-line UPS topology, but may include lower efficiency due to having multiple stages of power conversion. A line-interactive UPS topology may have a low cost, a simple design, and a highly reliable performance. While efficiency of the line-interactive UPS topology is greater than the on-line UPS topology, the line-interactive UPS topology does not provide output voltage regulation during operation.

The systems and methods described below may use a series-parallel line-interactive UPS topology with load leveling to address the aforementioned problems. A power supply system may provide peak power to one or more medical imaging loads to enable the one or more medical imaging loads to operate from an alternating current (AC) power rated lower than the peak power. For example, a system may include an AC-DC power converter that converts AC power from an AC transmission line to provide DC power on a DC bus used to power one or more medical imaging loads. The system may include a UPS system having a bidirectional DC-DC converter coupled to a battery. The bidirectional DC-DC converter may regulate the DC bus. The AC transmission line provides power to the medical imaging loads, and the DC-DC converter may provide additional power to the medical imaging loads during a pulsed load where the medical imaging load has an increased power demand corresponding to a scan performed by the medical imaging load. Further, the series-parallel line-interactive UPS topology, also known as universal or delta conversion, combines the advantages of the online and line-interactive characteristics and provides regulated output voltage and high efficiency with line conditioning characteristics.

Turning to the figures, FIG. 1 shows a power supply system 10 that provides power to one or more medical imaging loads 12 and/or other electronics 14. A main AC power source may provide power via an AC power line 16, such as a 20 kVA transmission line, coupled to an AC to direct current (DC) converter 18. The AC-DC converter 18, such as a high frequency power distribution unit (HFPDU), may convert the AC power to DC and provide the DC power, via a DC bus 20, to the medical imaging loads 12 and/or other electronics 14.

The AC-DC converter 18 and/or the UPS system 30 may be a smaller size and higher efficiency as compared to a three-phase AC online UPS due to the line-interactive topology of the AC-DC converter 18. For example, the AC-DC converter 18 and/or the UPS system 30 may be smaller due to having a single-phase single stage DC-DC conversion system compared to the three phase double conversion (AC-DC and DC-AC) of the AC online UPS. Further, the AC-DC converter 18 and/or the UPS system 30 may be smaller in size due to being rated lower than a peak power rating of the medical imaging loads 12 and/or other electronics 14 as compared to an AC-DC converter rated to provide the peak power rating.

While one or more medical imaging loads 12 are described below with respect to loads for a computed tomography (CT) system, it will be appreciated that embodiments are applicable for use with other imaging configurations. The one or more medical imaging loads 12 may include a high voltage generator 22 coupled to the DC bus 20. The high voltage generator 22 may provide power to an X-ray tube 24, such as a computed tomography (CT) imaging system. The X-ray tube 24 may emit X-ray beams toward a subject or object, such as a patient. The beam, after being attenuated by the subject, impinges upon an array of radiation detector. The intensity of the attenuated beam radiation received at the detector array may be dependent upon the attenuation of the X-ray beam by the subject. Each detector element of the detector array produces a separate electrical signal indicative of the attenuated beam received by each detector element. The electrical signals are transmitted to a data processing system for analysis which produces an image. Further, the X-ray source and the detector array may be rotated, via an axial drive and motor 26, about a gantry 28 within an imaging plane and around the subject or object. When the gantry 28 is rotated, it converts the power from the DC bus to rotational kinetic energy via the motor 26.

The DC bus 20 may be electrically coupled to a UPS system 30. The UPS system 30 may include a DC-DC bidirectional converter 32 to charge and discharge one or more batteries of a battery energy storage system (BESS) 34. Further, the DC-DC bidirectional converter 32 may establish and regulate the DC bus 20. That is, the AC power line 16 may provide support and power to the DC bus 20 but not control operation of the DC bus 20, such as regulating and maintaining the DC bus 20 to be at 700 Volts (V). In the event of power disruption (e.g., outages or faults), the DC-DC bidirectional converter 32 may provide power from the one or more batteries to the DC bus 20.

The UPS system 30 may be controlled by a control system 36 having a processor 38 or multiple processors and memory 40. The processor 38 may be operatively coupled to the memory 40 to execute instructions for carrying out the presently disclosed techniques. These instructions may be encoded in programs or code stored in a tangible non-transitory computer-readable medium, such as the memory 40 and/or other storage. The processor 38 may be a general purpose processor (e.g., processor of a desktop/laptop computer), system-on-chip (SoC) device, or application-specific integrated circuit, or some other processor configuration. The memory 40, in the embodiment, includes a computer readable medium, such as, without limitation, a hard disk drive, a solid state drive, diskette, flash drive, a compact disc, a digital video disc, random access memory (RAM), and/or any suitable storage device that enables the processor 38 to store, retrieve, and/or execute instructions and/or data. The memory 40 may include one or more local and/or remote storage devices.

The processor 38 may control the bidirectional converter 32 to provide power from the batteries to the DC bus 20. As described in detail below, the processor 38 may provide load power leveling (e.g., smoothing) when delivering power to the one or more medical imaging loads 12. Since the input and output voltages are DC, the transients are minimized. Further, the UPS system 30 may mitigate stability concern and reduce or eliminate synchronization delays and/or transients.

Figure 2:
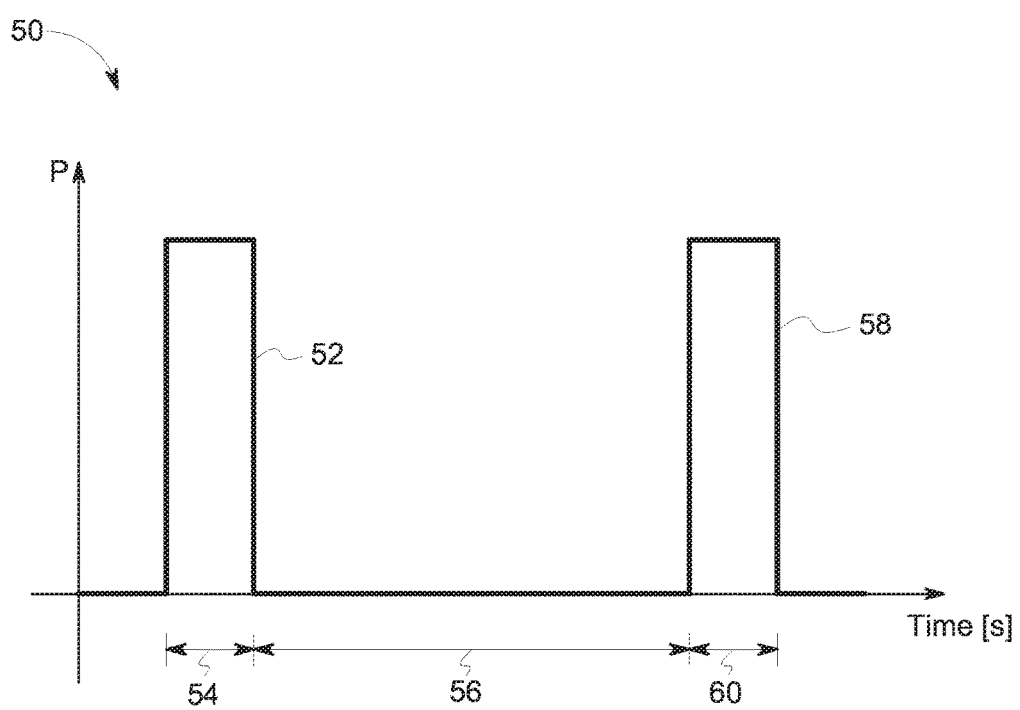
FIG. 2 is a graph of a pulsed load profile of a high voltage generator of the medical imaging load of FIG. 1, in accordance with an embodiment.

Referring to FIG. 2, a graph of a pulsed load profile of the high voltage generator 22 is illustrated having power demand of the load with respect to time. The high voltage generator 22 may operate as a constant power load (CPL) having a pulsed load 52. Further, the high voltage generator may have a pulsed load 52 such that a majority of the power is consumed in a pulse. The pulsed load 52 may correspond to power used by the X-ray tube to perform a scan. In some embodiments, the scan may be performed for a few seconds followed by a delay between scans. That is, the high voltage generator 22 may have pulses of power demand during a pulse period 54 and have a lower power demand during a standby period 56 that occurs for a longer period of time than the pulse period 56. After the standby period 56, the high voltage generator 22 may have another pulsed load 58 during a second pulse period 60.

While numbers are used in embodiments described herein, the numbers are simply used as examples. The UPS system 30 may be used with any medical imaging load suitable for having pulsed periods and standby periods. With this in mind, as an example, the pulse period 54 may be approximately 0.5-5 seconds (e.g., 2 seconds) and the standby period 56 between pulsed loads 52 and 58 may be approximately 50-500 (e.g., 200 seconds), bearing in mind that the longer period 56 and pulse period 54 may not be illustrated to scale in FIG. 2. Further, the X-ray tube 24 may have an average power demand of 10 kW or less and have a peak power demand during the pulsed load 52 of 50-200 kilowatts (kW) (e.g., 140 kW). As such, the high voltage generator 22 may have periodic peak power demands of pulsed loads 52 and 58 with longer periods of low power demands, such as approximately zero kW or less than 10 kW, between the pulsed loads 52 and 58. As such, less than 15% of the peak load may be supplied from the AC power grid.

The UPS system 30 may operate in various modes based on the load profile (e.g., during the pulse period 54 or the standby period 56), charge state of the BESS, and connection to the main AC source, such as a load leveling mode, a standby mode, an online mode, and a UPS mode.

The UPS system 30 may operate in load leveling mode (i.e. discharging mode) during the pulse periods. For example, during the load leveling mode, the high voltage generator 22 may have a power demand of 140 kW for 2 seconds, and the UPS system 30 may discharge power from the BESS 34 through the DC-DC bidirectional converter 32 to the one or more medical imaging loads 12. In this example, the AC power line 16 may deliver 20 kW constant power and the BESS 34 may deliver 130 kW through the DC-DC converter 32 for a total of 150 kW to match the total power demand of the one or more loads 12 (e.g., 140 kW for the high voltage generator 22 and 10 kW to an auxiliary load, such as the other electronics 14).

The UPS system 30 may operate in a standby mode (i.e. charging mode) where the power demand is primarily auxiliary loads (e.g., a power demand of approximately 10 kW or below from the other electronics 14). In the example above, the AC power line 16 may deliver 10 kW to the auxiliary load and deliver 10 kW to charge the BESS when the BESS is not fully charged. During standby mode the UPS system 30 may regulate the DC bus 20.

The UPS system 30 may operate in an online mode (i.e. charged mode) when the battery is fully charged and does not accept further energy. When the UPS system 30 is operating in the online mode, the AC-DC converter 18 may be in charge of regulation of the DC bus 20. That is, the rectifier operates in a voltage mode to maintain the DC bus 20 voltage constant while providing power to the auxiliary load.

The UPS system 30 may operate in a UPS mode (i.e. backup power supply mode) when the system is disconnected from the main AC power source and the BESS provides the entire load profile for a predetermined time until the main AC power source returns. The DC-DC converter provides the power from the BESS 34 to the load and simultaneously regulates the DC bus 20.

BESS 34 may include one or more lithium-ion (Li-ion) nickel cobalt aluminum (NCA) and/or lithium iron phosphate (LFP) cells. That is, the BESS 34 cells may perform discharging at up to 10 C. Further, LFP cells of the BESS 34 may be configured to withstand pulsed discharging up to 15 C for less than 5 seconds. For instance, each LFP cell rated for 3.3 VDC and 30 Ah, may be designed for pulsed discharging with high rate current up to 450 A for 2 seconds. Additionally, two Li-ion LFP based battery modules may include 108 cells connected in series (each contains 54 series) will deliver 350 VDC, 10 kWh energy and peak power of 150 kW for 2 second to the DC link.

To prevent overcharging, overheating, and/or depth of discharge, the BESS 34 may be controlled by a battery management system (BMS) to monitor and control the voltage, temperature, and state of charge (SOC) status of each cell and whole module accordingly in order to provide a longer lifespan and safer performance. The BMS may be included in the control system 36 or a separate control system.

The BMS may include a modular or master-slave type architecture. Further, the BMS may include data acquisition slave cards that collect voltage and temperature of each cell and send it to the master card which monitors the voltage and temperature of each cell in order to be at the predefined range of safe operation and turns on the balancing circuits or fans if required. This master card also communicates with the higher level control of the whole system to report the status of the module and also exchanges some safety and protection handshaking signals.

Figure 3:
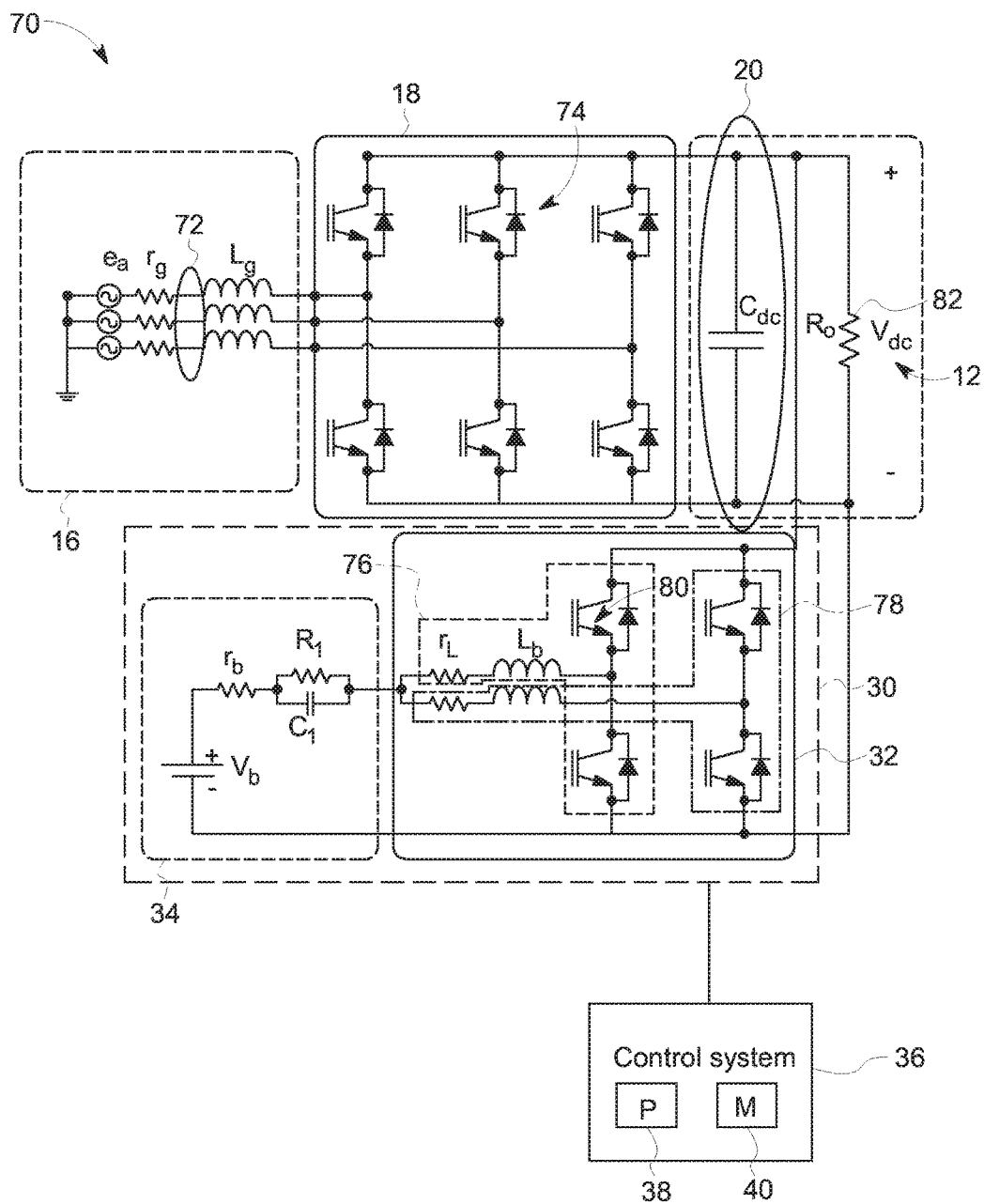
FIG. 3 is a schematic diagram of a circuit of the uninterruptible power supply system of FIG. 1, in accordance with an embodiment.

FIG. 3 is a circuit diagram 70 of the power supply system 10 having the AC power line 16, the AC-DC converter 18, the DC bus 20, the one or more loads 12, and the UPS system 30 operating in standby mode. The AC-DC converter 18 may rectify three phases 72 of power from the AC power line 16 to deliver a constant power to the DC bus 20. The AC-DC converter 18 may include a three-phase voltage source rectifier (VSR) 74. When operating in standby mode, the DC-DC bidirectional converter 32 regulates voltage of the DC bus 20 and the VSR operates in current mode and delivers 20 kW active power to the DC bus at unity power factor.

The processes described below may be stored in the memory 40 of the system 10 and executed as instructions by the processor 38 (e.g., running code). The processor 38 may send signals to control one or more switches 80 of the DC-DC bidirectional converter 32 to cause the switches to open and/or close to charge or discharge the BESS 34. That is, the processor 38 may control the one or more switches 80 based on a duty cycle that enables the DC-DC bidirectional converter 32 to act as a buck-boost converter that boosts voltages from the BESS 34 to voltages of the DC bus 20 when discharging and bucks voltages from the DC bus 20 to voltages of the BESS 34 when charging.

Further, by sending signals to control operation of the one or more switches 80, the processor 38 may establish and regulate the voltage on the DC bus 20 when the UPS system 30 is operating in load leveling mode, standby mode, or UPS mode. The DC-DC bidirectional converter 32 may include a first leg 76 and a second leg 78. Due to a duty cycle of the switches 80 DC-DC bidirectional converter 32, the processor 38 may send signals to control the switches 80 to cause a two phase interleaved configuration that minimizes an inductance current ripple by having a 180 degree phase-shift between currents through the first leg 76 as compared to currents through the second leg 78. The power from the DC bus 20 may then be delivered to the one or more loads 12 represented in the circuit diagram 70 as a resistor 82 $R_o$.

Figure 4:
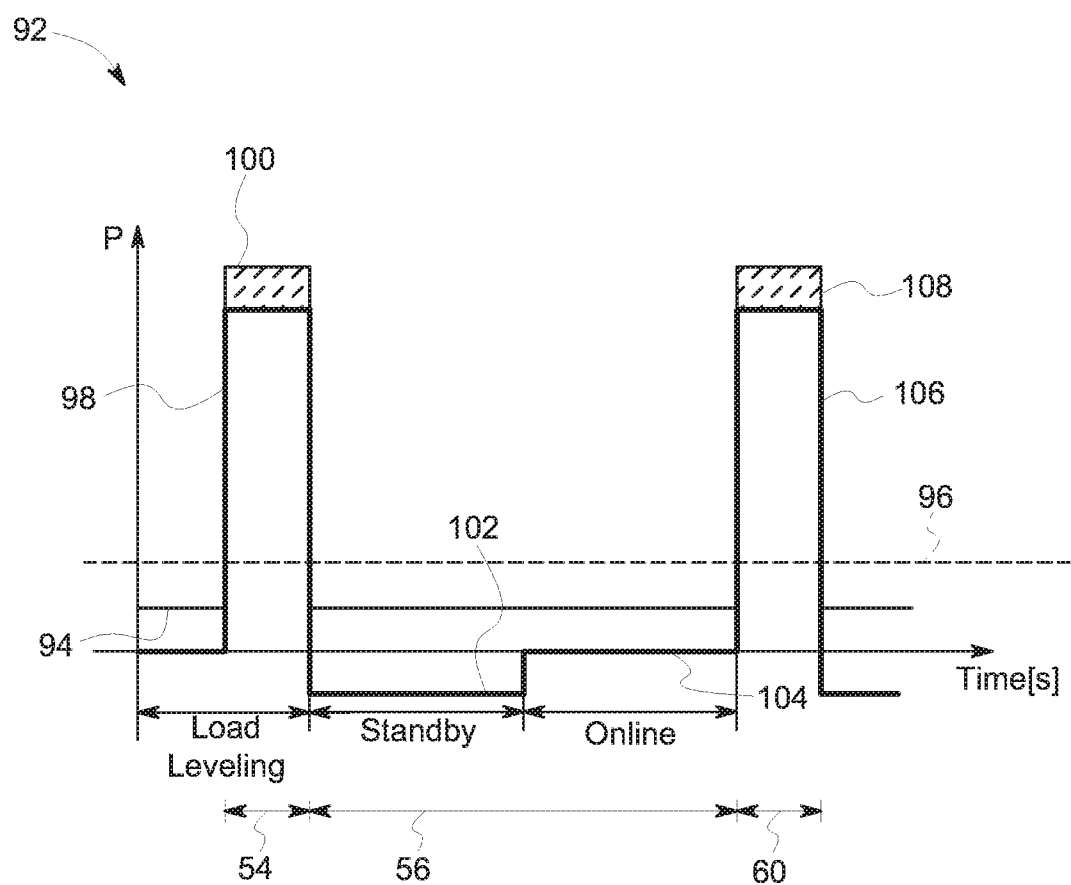
FIG. 4 is a graph of power provided by the UPS of FIG. 1 to the pulsed load profile of FIG. 2, in accordance with an embodiment.

FIG. 4 is a graph 92 of the load profile of power demanded by the one or more loads 12 as well as the power provided by the AC power line 16 and the BESS 34. The processor 38 may control operation of the UPS system 30 to provide power based on power demand of the one or more loads 12 and operation of the main AC power source. As mentioned above, the system 10 may include an auxiliary load having a constant power demand of 10 kW, referred to as a constant voltage load (CVL), as indicated by line 94. Further, the AC power line 16 may provide 20 kW of power as indicated by line 96. To account for the pulsed load 52 of FIG. 2 of the high voltage generator 22 as well as the auxiliary load, the processor 38 may send signals to the switches 80 to cause the BESS 34 to provide power, via the DC-DC bidirectional converter 32, to the high voltage generator 22 and the auxiliary load. The pulsed power 98 provided by the BESS 34 and the constant power 100 provided by the AC power line 16 may match the load profile of the pulsed load 52 of FIG. 2. In this example, the 20 kW from AC power and 130 kW from the BESS 34 may match the 140 kW power demand of the pulsed load 52 and the 10 kW of the auxiliary load. By charging the BESS 34 during non-pulsed load periods (e.g., standby period 56), the UPS system 30 may provide peak loads greater than the peak power rating of the UPS system 30. Further, in some embodiments, a majority of peak load power (e.g., 50%, 80%, or more) may be provided to the one or more loads 12 via charging and discharging of the UPS system 30.

After operating in load leveling mode, the processor 38 may send one or more signals to cause the switches to open or close such that the BESS 34 is recharged by power provided from the AC power line 16 indicated by line 102. Further the AC power line 16 may provide power to the auxiliary load while recharging the BESS 34. When the BESS 34 is fully charged, the DC-DC converter may not accept further power from the AC power line as indicated by line 104. Then at period 60, the processor 38 may control the switches 80 again to enable power from the BESS 34 and the AC power line 16 to meet power demand during another pulsed load as indicated by pulsed power 106 and constant power 108.

The high voltage generator pulsed load in load leveling mode may have a negative incremental impedance characteristic of the CPLs in which although an instantaneous value of impedance is positive, an incremental impedance is negative.

Figure 5:
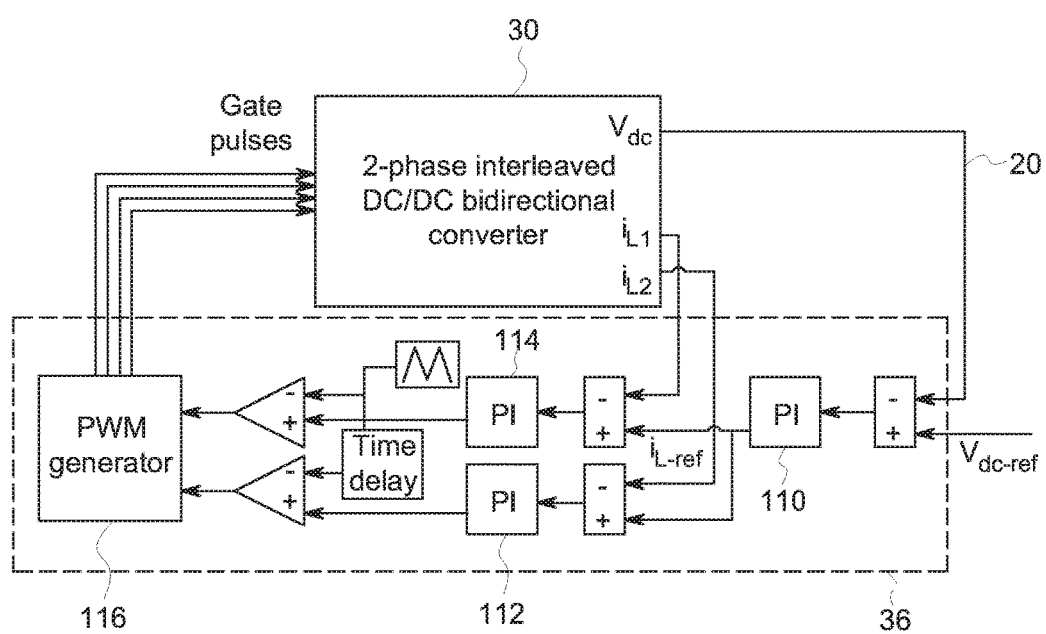
FIG. 5 is a diagram of the dual-loop control scheme for the DC/DC converter, in accordance with an embodiment.

FIG. 5 shows a block diagram of a dual loop control scheme implemented by the control system 36 to control the DC-DC bidirectional converter 32 to regulate the voltage of the DC bus 20. The control scheme may be performed by the processor 38 (e.g., running code) to control operation of the switches 80 of the bidirectional converter. While the dual loop control scheme is described in detail below, other control schemes, such as a constant frequency sliding mode controller (CFSMC) may be used as a nonlinear control system. For example, the control system 36 may include a CFSMC controller that receives signals related the voltage of the BESS, the capacitor $C_{DC}$, and/or the resistor 82 to provide signals based on a continuous function and a switching function that accounts for disturbances of the BESS, the capacitor $C_{DC}$, and/or the resister 82 during the control.

In FIG. 5, as an example, the control system 36 may employ a simple dual-loop control method to regulate the DC link voltage, independent of variation of the BESS terminal voltage and the load, and simultaneously charge the BESS. Moreover, the control system 36 may monitor, via the inductance current ripple $i_{L1}$ and $i_{L2}$, the battery charging current. Further, the inductance current ripple $i_{L1}$ and $i_{L2}$ is much lower, as compared to one leg bidirectional DC-DC converters, to ensure the lowest amount of current ripples and improve the lifespan of the battery and the BESS as well. In this technique, the faster inner loop manages two inductance currents while the slower outer loop regulates the DC bus voltage.

The control system 36 may include one or more proportional-integral-derivative controllers that are used to determine gate pulses to regulate the DC bus voltage. For example, the control system 36 may monitor a DC bus voltage $V_{DC}$ (e.g., voltage across capacitor $C_{DC}$ as shown in FIG. 3) and determine, via a proportional-integral-derivative (PID) controller 110, a reference current $i_{L-ref}$ by comparing the DC bus voltage $V_{DC}$ to a reference voltage $V_{DC-ref}$. Although a PID controller is used herein, this is merely an example, and any suitable controller (e.g., proportional-integral, proportional-derivative) may be used. The reference current may indicate a desired current through the first and second legs 76 and 78 to maintain the desired DC bus voltage. Further, the control system 36 may compare, via PID controllers 112 and 114, the reference current $i_{L-ref}$ and the measured current $i_{L1}$ and $i_{L2}$ through the first and second legs 76 and 78, respectively to determine an error. The error may then be used, via a PWM generator 116, to generate the one or more signals to send to the one or more switches 80 to enable the processor 38 to regulate the DC bus voltage. Further, the method may include a time delay to reduce overshoots and undershoots of the voltage.

Referring back to FIG. 3, when the UPS system 30 is operating in standby mode, the following equations can be derived to describe the DC-DC bidirectional converter 32:

$$L_{eq}\frac{d}{dt}i_b = -r_{eq}i_b - dv_{dc} - v_{c1} + v_b \quad (1)$$

where $v_b$ is the BESS 34 modeled as a DC source, $r_b$ is an internal resistance of the BESS 34, $i_b$ is the battery current (considering discharging current as reference direction), and also it is one of the states ($x=[i_b v_{dc} i_d i_q v_{c1}]^T$). $L_{eq}$ and $r_{eq}$ are the equivalent inductance ($L_{eq}=L_b/2$) and resistance ($r_{eq}=r_b+r_L/2$) of the DC converter and d is the duty ratio (d+d'=1).

Dynamic behavior of the DC link is described in the following equation:

$$C_{dc}\frac{d}{dt}v_{dc} = di_b + \frac{3}{2}m_d i_d + \frac{3}{2}m_q i_q - \frac{v_{dc}}{R_o} \quad (2)$$

where $v_{dc}$ is the DC link voltage or voltage across the capacitor, $C_{dc}$. Variables $i_d$, $i_q$, $m_d$ and $m_q$ are direct and quadrature components of the grid currents and modulation indexes, respectively.

The AC-DC rectifier may be represented with the following equations:

$$L_g\frac{d}{dt}i_d = -r_g i_d + L_g \omega i_q - m_d v_{dc} + e_d \quad (3)$$

$$L_g\frac{d}{dt}i_q = -r_g i_q - L_g \omega i_d - m_q v_{dc} \quad (4)$$

where in a dq0 rotating reference frame in which d-axis of dq reference frame is aligned with the grid voltage vector ($e=[e_d, e_q]^T$), so hence the q component of the grid voltage vector become zero ($e_q=0$). The Li-ion battery energy storage is modeled by an internal resistance, $r_b$, and an RC parallel network, $R_1$ and $C_1$, representing the time constant or transient response of the battery.

Behavior of the BESS 34 is represented by the following equation:

$$C_1\frac{d}{dt}v_{c1} = i_b - \frac{v_{c1}}{R_1} \quad (5)$$

where an RC parallel network, $R_1$ and $C_1$, represents the time constant or transient response of the battery. Further, $v_{c1}$ is a voltage across the capacitance.

Figure 6:
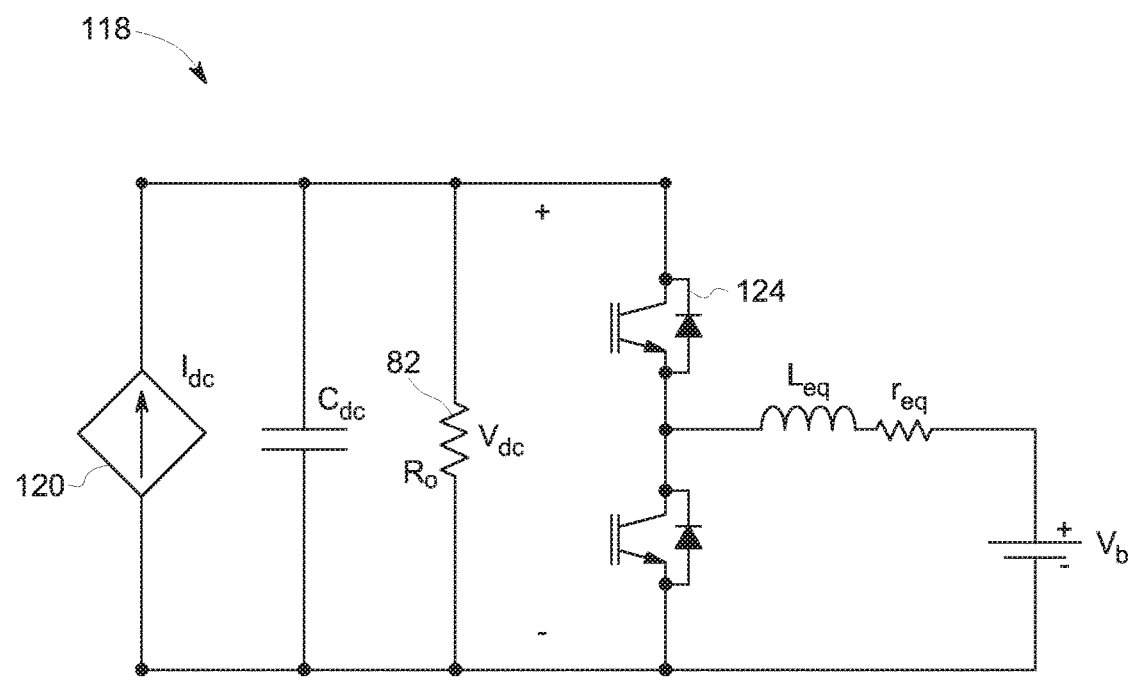
FIG. 6 is a schematic diagram of a simplified model of a circuit of the uninterruptible power supply of FIG. 1.

FIG. 6 is a simplified circuit diagram of the circuit diagram 70 described with respect to FIG. 3. To reduce the model of the system, the AC part, including the AC power line 16 and the AC-DC converter 18 which may be controlled in current mode to deliver a constant power, can be modeled by a constant current source 94 injecting $I_{dc}$ to the DC bus 20. The BESS 34 and parts of the DC-DC bidirectional converter 32 may also represented by a constant voltage and internal resistance and inductance equivalence. Then the system is reduced to a 2$^{nd}$ order state space model and the dynamic model of the system in mode II can be represented as:

$$L_{eq}\frac{d}{dt}i_b = -r_{eq}i_b - dv_{dc} + v_b \quad (6)$$

$$C_{dc}\frac{d}{dt}v_{dc} = -di_b - \frac{v_{dc}}{R_o} + i_{dc} \quad (7)$$

Equations (6) and (7) present a nonlinear system. By means of small signal analysis around operating points while considering small disturbances as well:

$$i_b I_b + \tilde{i}_b$$

$$v_{dc}=V_{dc}+\tilde{v}_{dc}$$

$$d=D+\tilde{d}$$

$$v_b=V_b+\tilde{v}_b$$

$$i_{dc}=I_{dc}+\tilde{i}_{dc} \quad (8)$$

where $I_b$, $V_{dc}$, D, $V_b$ and $I_{dc}$ are the average values of $i_b$, $v_{dc}$, d, $v_b$ and $i_{dc}$, respectively. By substituting (8) into (6) and (7), the model may be represented as $$L_{eq}\frac{d}{dt}\tilde{i}_b = -r_{eq}\tilde{i}_b - D\tilde{v}_{dc} - V_{dc}\tilde{d} + \tilde{v}_b \quad (9)$$

$$C_{dc}\frac{d}{dt}\tilde{v}_{dc} = -D\tilde{i}_b - I_b\tilde{d} - \frac{\tilde{v}_{dc}}{R_o} + \tilde{i}_{dc} \quad (10)$$

The transfer functions of the duty-to-output voltage, $G_{vd}(s)$, and duty-to-battery current, $G_{id}(s)$ are presented in (11) and (12), respectively.

$$G_{vd}(s) = \frac{\tilde{v}_{dc}(s)}{\tilde{d}(s)} = \frac{1}{L_{eq}C_{dc}} \cdot \frac{\frac{L_{eq}}{D}\left(\frac{V_{dc}}{R_o} - I_{dc}\right)s - V_b}{s^2 + \left(\frac{r_{eq}}{L_{eq}} + \frac{1}{R_o C_{dc}}\right)s + \frac{D^2}{L_{eq}C}} \quad (11)$$

$$G_{id}(s) = \frac{\tilde{i}_b(s)}{\tilde{d}(s)} = \frac{1}{L_{eq}C_{dc}} \cdot \frac{V_{dc}C_{dc}s + \left(\frac{2V_{dc}}{R_o} - I_{dc}\right)}{s^2 + \left(\frac{r_{eq}}{L_{eq}} + \frac{1}{R_o C_{dc}}\right)s + \frac{D^{2q}}{L_{eq}C}} \quad (12)$$

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A system comprising:
an alternating current (AC)-direct current (DC) converter configured to convert power from an AC supply to a DC bus to provide a first portion of power to a medical imaging load;

an uninterruptible power supply (UPS) coupled to the DC bus, wherein the UPS comprises:
at least one battery cell; and
a DC-DC converter comprising one or more switches and coupled between the at least one battery cell and the DC bus; and
a control system comprising a processor configured to send one or more signals to control operation of the one or more switches to cause the DC-DC converter to control power discharged from the at least one battery cell to the DC bus to provide a second portion of power to the medical imaging load;
wherein the DC bus is directly coupled to the medical imaging load and is configured to provide the first and second portions of power to the medical imaging load as DC power.

2. The system of claim 1, the processor is configured to provide the second portion of power to match a pulsed load profile of power demand of the medical imaging load.

3. The system of claim 1, wherein the processor is configured to control operation of the switches to regulate a voltage of the DC bus.

4. The system of claim 1, wherein the processor is configured to control the one or more switches to cause the DC-DC converter to:
charge the at least one battery cell, via power from the AC supply, during a charging period; and
discharge power from the at least one battery cell during a pulsed load period, wherein the pulsed load period comprises an increased power demand of the medical imaging load.

5. The system of claim 1, wherein the processor is configured to control the one or more switches to cause the DC-DC converter to operate as a backup power supply and to provide power to match power demand of the medical imaging load for a period of time while the AC supply is unavailable.

6. The system of claim 1, wherein the DC-DC converter comprises a DC-DC bidirectional converter configured to charge the at least one battery cell in a first direction and discharge the at least one battery cell in a second direction.

7. The system of claim 1, wherein the at least one battery cell is configured to provide a majority of the power to meet the power demand during a pulsed load.

8. The system of claim 1, wherein the medical imaging load comprises a computed tomography (CT) imaging system.

9. The system of claim 1, wherein the UPS is configured to operate in a load leveling mode, a standby mode, an online mode, and a UPS mode, and the processor is configured to regulate the DC bus during the load leveling mode, the standby mode, and the UPS mode, and the AC-DC converter is configured to regulate the DC bus during the online mode.

10. A system configured to provide power to a medical imaging load, comprising:
an uninterruptible power supply (UPS) configured to couple to a direct current (DC) bus, comprising:
at least one battery cell; and
a DC-DC converter configured to convert power from a supply that supplies power to the medical imaging load, via the DC bus, to charge the at least one battery cell, and to convert power from the at least one battery cell to discharge power to provide additional power to the medical imaging load,
wherein the additional power provided to the medical imaging load is DC power.

11. The system of claim 10, wherein the DC-DC converter is configured to provide additional power to the medical imaging load corresponding to a scan of the medical imaging load.

12. The system of claim 11, wherein the DC-DC converter is configured to provide a majority of power to the medical imaging load from the at least one battery cell during the scan.

13. The system of claim 10, wherein the DC-DC converter is configured to regulate power on the DC bus when the UPS is in a load leveling mode, a standby mode, and an online mode.

14. The system of claim 10, wherein the DC-DC converter comprises a first leg and a second leg configured to operate with currents having a 180 degree phase-shift between one another to minimize an inductance current ripple through the converter.

15. The system of claim 10, wherein the UPS is configured to provide the additional power to match a pulsed load profile of power demand of the medical imaging load.

16. The system of claim 10, the DC-DC converter is configured to charge the at least one battery cell during a charging period and to discharge power from the at least one battery cell during a pulsed load period that corresponds to an increased power demand of the medical imaging load during a scan.

17. A method, comprising:
directly electrically coupling a direct current (DC) bus to a medical imaging load;
electrically coupling the DC bus to an alternating current (AC)-DC converter configured to convert power from an AC supply to the DC bus to provide a first portion of power to the medical imaging load; and
electrically coupling an uninterruptible power supply (UPS) to the DC bus, wherein the UPS comprises at least one battery cell and a DC-DC converter comprising one or more switches, and wherein the DC-DC converter is configured to control power discharged from the at least one battery cell to the DC bus to provide a second portion of power to the medical imaging load corresponding to a pulsed load profile of the medical imaging load, wherein the DC bus is configured to provide the first and second portions of power to the medical imaging load as DC power.

18. The method of claim 17, wherein the pulsed load profile corresponds to an image scan of the medical imaging load.

19. The method of claim 17, comprising electrically coupling a high frequency power distribution unit between the AC supply and the DC bus.

20. The method of claim 17, comprising electrically coupling a high voltage generator between the DC bus and the medical imaging load.

* * * * *